(12) United States Patent
Duffy et al.

(10) Patent No.: US 6,187,393 B1
(45) Date of Patent: Feb. 13, 2001

(54) LIQUID CRYSTAL ALKENYL BICYCLO [2.2.2]OCTANES AND MIXTURES AND DEVICES CONTAINING SUCH COMPOUNDS

(75) Inventors: Warren L. Duffy; Stephen M Kelly; John W Goodby, all of Hull (GB)

(73) Assignee: The Secretary of State for Defence in Her Britannic Majesty's Government of the United Kingdom of Great Britain and Northern Ireland, Hampshire (GB)

( * ) Notice: Under 35 U.S.C. 154(b), the term of this patent shall be extended for 0 days.

(21) Appl. No.: 09/269,110

(22) PCT Filed: Sep. 22, 1997

(86) PCT No.: PCT/GB97/02568
§ 371 Date: Mar. 19, 1999
§ 102(e) Date: Mar. 19, 1999

(87) PCT Pub. No.: WO98/13326
PCT Pub. Date: Apr. 2, 1998

(30) Foreign Application Priority Data

Sep. 26, 1996 (GB) .................................................. 9620108

(51) Int. Cl.$^7$ ......................... C09K 19/32; C07C 43/188; C07D 319/06; C07D 239/34; G02F 1/1333
(52) U.S. Cl. ................ 428/1.1; 252/299.62; 252/299.63; 544/335; 546/350; 549/369; 560/120
(58) Field of Search ......................... 252/299.62, 299.63; 544/335; 546/339, 341, 350; 549/369; 568/657, 667, 669; 560/104, 113, 120; 428/1.1; 349/179

(56) References Cited

U.S. PATENT DOCUMENTS 4,261,652 * 4/1981 Gray et al. ....................... 252/299.62

FOREIGN PATENT DOCUMENTS

| 2 071 649 | 9/1981 | (GB) . |
| 87 01113 | 2/1987 | (WO) . |
| 87 07290 | 12/1987 | (WO) . |

OTHER PUBLICATIONS

Gray G W Et Al: "The Effects of Variation of a Core Ring System in the Mesogenic Side Chain of Liquid–Crystal Polysiloxnanes" Makromolekular Chemie, Macromolecular Chemistry and Physics, vol. 191, No. 10, Oct. 1, 1990, pp. 2227–2235, XP000205327 see whole document.

* cited by examiner

Primary Examiner—Shean C. Wu
(74) Attorney, Agent, or Firm—Nixon & Vanderhye

(57) ABSTRACT

Compounds of formula (I)

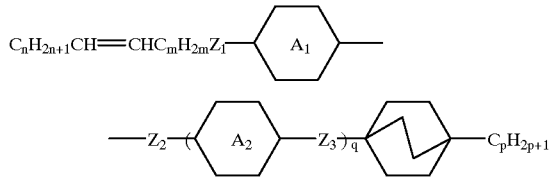

are provided which are particularly useful in super twisted nematic devices, where n may be 0–5; m may be 0–5; p may be 1–9; q may be 1, 1, or 2; $A_1$, $A_2$ are independently chosen from 1–4, -disubstituted benzene, 2,5-disubstituted pyrimidine, or 2,5-disubstituted pyridine, trans- 1,4-disubstituted cyclohexane, trans- 2,5-disubstitued dioxane. The aromatic rings may be laterally substituted with F, Cl, Br or CN; $Z_1$ may be O, COO, OOC; $Z_2$, $Z_3$ are independent chosen from a direct bond, COO, OOC, $C_2H_4$, $CH_2O$, $OCH_2$, or -c≡c-, provided that when $Z_1$ is O and m is 1, 3 or 5 the carbon—carbon double bond configuration is E; provided that when $Z_1$ is O and m is 2 or 4 the carbon—carbon double bond configuration is Z; provided that when $Z_1$ is COO or OOC and m is 0, 2 or 4 the carbon—carbon double bond configuration is E; and provided that when $Z_1$ is COO or OOC and m is 1, 3 or 5 the carbon—carbon double bond configuration is Z.

8 Claims, 1 Drawing Sheet

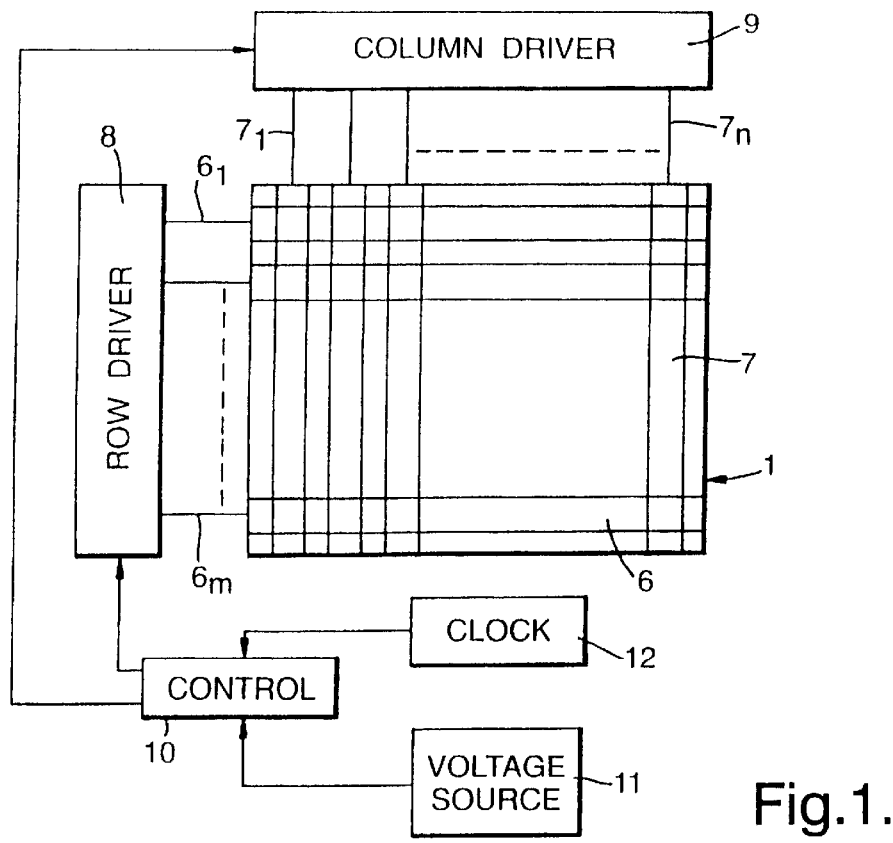
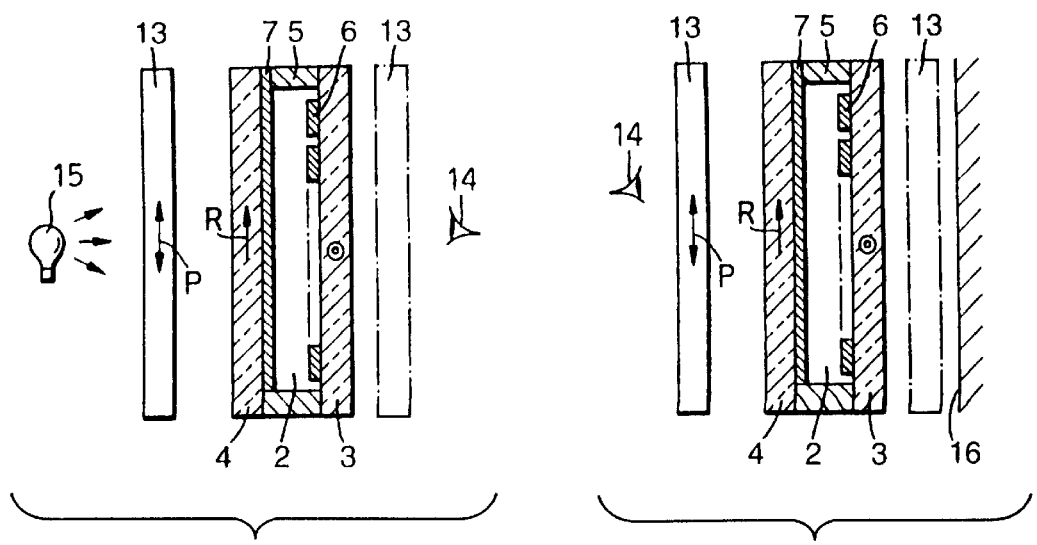
Fig.1.
Fig.2.
Fig.3.

LIQUID CRYSTAL ALKENYL BICYCLO [2.2.2]OCTANES AND MIXTURES AND DEVICES CONTAINING SUCH COMPOUNDS

This is a 35 U.S.C. § 371 of PCT/GB97/02568, filed Sep. 22, 1997.

The present invention describes new compounds. In particular it describes compounds for use in liquid crystal mixtures and in liquid crystal displays (LCDs) or in applications relating to inter alia thermography utilising nematic liquid crystal or chiral nematic liquid crystal mixtures.

BACKGROUND OF THE INVENTION

LCDs, such as multiplexed Twisted Nematic TN-LCDs, Super Twisted Nematic STN-LCDs, Super Birefringent SBE-LCDs, Electrically Controlled Birefringence ECB-LCDs or flexoelectric LCDs are currently used or being developed for computer monitors, laptop or notebook computers, portable telephones, personal digital assistants, etc. The optical, electrical and temporal performance, e.g., contrast, threshold and driving voltages, and response times, of such displays depends crucially on the ratios of the elastic constants ($k_{33}$, $k_{22}$, $k_{11}$). Currently commercially available nematic mixtures for sophisticated high-information-content LDCs, such as STN-LCDs, generally incorporate trans-1,4-disubstituted-cyclohexyl derivatives with a terminal alkenyl chain (i.e., incorporating a carbon—carbon double bond) directly attached to the cyclohexane ring in order to produce the necessary elastic constant ratios for short response times, high multiplexing rates and low driving voltages. Such materials are costly and difficult to synthesise due to the requirement for a trans configuration of the 1,4-disubstituted cyclohexane ring and the necessity of synthesising the carbon—carbon double bond stepwise from this trans-1,4-disubstituted-cyclohexyl intermediate. If the carbon—carbon double bond is substituted at both carbon atoms, it must have a trans (E) configuration in order to exhibit an advantageous combination of elastic constants and to have an acceptably high nematic-isotropic transition temperature (N-1). The trans configuration is then generally produced by isomerisation of the cis (Z) form generated by the preceding Wittig reaction.

Light crystalline bicyclo[2.2.2]octanes are known and are described in for example G W Gray et al, J. Chem. Soc. Perkin II, (1981), pp 26–31, N Carr et al (1981), Vol 66, pp 267–282, (1985), Vol 129, pp 301–313, R Dabrowski, Mol. Cryst. Liq. Cryst., (1991), Vol 209, pp 201–211, R Dabrowski, Ferroelectrics., (1991), Vol 114, pp 229–240.

For all the above applications it is not usual for a single compound to exhibit all of the properties highlighted, normally mixtures of compounds are used which when mixed together induce the desired phases and required properties.

BRIEF DESCRIPTION OF THE DRAWINGS

FIG. 1 is a plan view of a matrix multiplex addressed liquid crystal display with associated drivers and controls;

FIG. 2 is a cross-section of a display such as in FIG. 1 used in a transmissive mode; and FIG. 3 is a cross-section of a display such as in FIG. 1 used in a reflective mode.

According to this invention compounds are provided of Formula I:

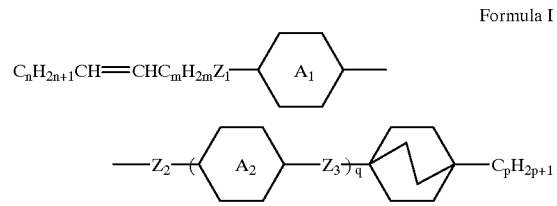

Formula I wherein:

n may be 0–5;

m may be 1–5;

p may be 1–9;

q may be 0, 1 or 2;

$A_1$, $A_2$ are independently chosen from 1,4-disubstituted benzene, 2,5-disubstituted pyrimidine, or 2,5-disubstituted pyridine, trans-1,4-disubstituted cyclohexane, trans-2,5-disubstituted dioxane; the aromatic rings may be laterally substituted with F, Cl, Br or CN;

$Z_1$ may be O, COO, OOC;

$Z_2$, $Z_3$ are independently chosen from a direct bond, COO, OOC, $C_2H_4$, $CH_2O$, $OCH_2$ —c≡c—;

provided that when $Z_1$ is O and m is 1, 3 or 5 the carbon—carbon double bond configuration is E; provided that when $Z_1$ is O and m is 2 or 4 the carbon—carbon double bond configuration is Z; provided that when $Z_1$ is COO or OOC and m is 0, 2 or 4 the carbon—carbon double bond configuration is E; and provided that when $Z_1$ is COO or OOC and m is 1, 3 or 5 the carbon—carbon double bond configuration is Z.

The structural and other preferences are expressed below on the basis of inter alia desirable liquid crystalline characteristics, in particular advantageous elastic constant ratios or flexoelectric coefficients in the nematic phase, a wide nematic phase with a high nematic-isotropic liquid transition temperature, low smetic tendencies and ready synthesis from commercially available starting materials already incorporating the carbon—carbon double bond with the desired configuration and position.

Preferably n is 1–3; Preferably m is 1–3; Preferably n+m is ≦7; Preferably p is 3–7; Preferably q is 0 or 1; Preferably $A_1$ is 1,4-disubstituted benzene; Preferably $A_2$ is trans- 1,4-disubstituted cyclohexane; Preferably $Z_1$ is O or COO; Preferably $Z_2$ and $Z_3$ are direct bonds.

Overall preferred structures for formula I are those listed below:

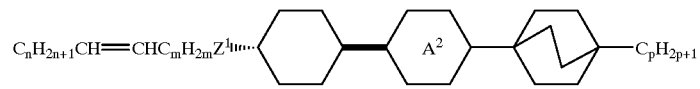

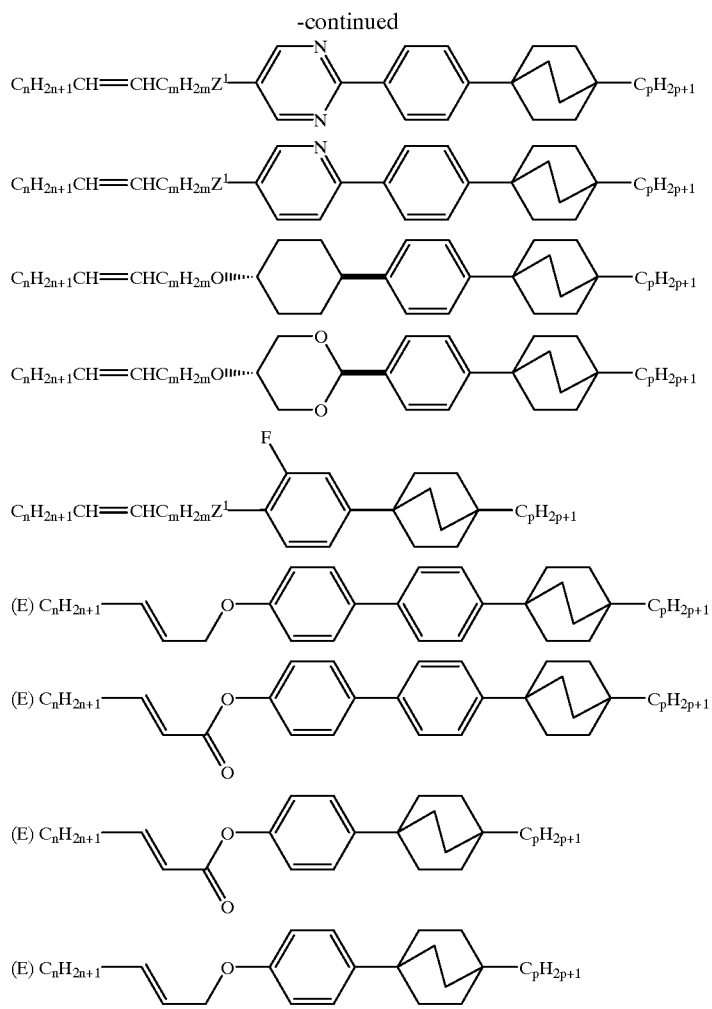

Compounds of formula I can be prepared by various routes. Typically the ethers can be prepared by the Mitsunobu reaction (Synthesis, (1981) pp 1) of a phenol with an alkenyl in the presence of triphenyl phosphine, a dehydrating agent, such as diethyl azodicarboxylate, and a suitable solvent, such as tetrahydrofuran or N,N'-dimethylformamide. Alternatively they can be synthesised by alkylation of a secondary alcohol or phenol with the tosylate of the appropriate alkenol in the presence of a suitable base, such as potassium tert.-butoxide, and a suitable solvent, such as tert.-butyl-methyl ether or 1,2-dimethoxyethane (J. Mater. Chem., (1994) Vol. 4, pp 1673). The esters can be prepared by esterification (Angewandte Chemie (1978) Vol. 90, pp 556) of the appropriate phenol or secondary alcohol with an alkenoic acid in the presence of 4-(dimethylamino)pyridine, a dehydrating agent, such as N,N'-dicyclohexylcarbodiimide, and a suitable solvent, such as dichloromethane or N,N'-dimethylformamide. Alternatively they can be synthesised by esterification of the appropriate phenol or secondary alcohol with an alkenoic acid chloride (produced, for example, from the corresponding alkenoic acid by the action of thionyl chloride or oxalyl chloride) in the presence of a base, such as pyridine or triethylamine, and a suitable solvent, such as toluene or dichloromethane.

In the following examples C signifies the crystalline state, N the nematic phase, I the isotropic phase and $\Delta T_{NI}$ the temperature range of the nematic phase.

The invention will now be described, by way of example only, with reference to the following examples and diagrams:

DETAILED DESCRIPTION OF THE INVENTION

EXAMPLE 1

Preparation of 1-(4-[(E)-hex-2-enyloxy]phenyl)-4-pentylbicyclo[2.2.2]octane

Triphenylphosphine (0.34 g, 0.0013 mol) was added in small portions to a solution of (E)-hex-2-en-1-ol (0.13 g, 0.0013 mol), 4-(4-pentylbicyclo[2.2.2]octyl)phenol (0.35 g, 0.0013 mol), diethylazodicarboxylate (0.22 g, 0.0013 mol) in dry tetrahydrofuran (20 cm$^3$), cooled in an ice bath under an atmosphere of nitrogen. The reaction mixture was stirred at room temperature overnight. The solvent was removed under reduced pressure and the crude product was purified by column chromatography on silica gel using a 9:1 petroleum ether (40–60° C./ethyl acetate mixture as eluent, followed by recrystallisation from ethanol to yield 0.18 g (39%), K 69° C., S$_A$-N 59° C., N-I 134° C.

The following compounds could be obtained analogously: 1-(4-[(E)-But-2-enyloxy]phenyl)-4-propylbicyclo[2.2.2] octane. 1-(4-[(E)-Pent-2-enyloxy]phenyl)-4-propylbicyclo [2.2.2]octane. 1-(4-[(E)-Hex-2-enyloxy]phenyl)-4-propylbicyclo[2.2.2]octane. 1-(4-[(E)-Hept-2-enyloxy]

phenyl)-4-propylbicyclo[2.2.2]octane. 1-(4-[(E)-Oct-2-enyloxy]phenyl)-4-propylbicyclo[2.2.2]octane. 1-(4-[(E)-But-2-enyloxy]phenyl)-4-pentylbicyclo[2.2.2]octane. 1-(4-[(E)-Pent-2-enyloxy]phenyl)-4-pentylbicyclo[2.2.2]octane. 1-(4-[(E)-Hept-2-enyloxy]phenyl)-4-pentylbicyclo[2.2.2]octane. 1-(4-[(E)-Oct-2-enyloxy]phenyl)-4-pentylbicyclo[2.2.2]octane. 1-(4-[(E)-But-2-enyloxy]phenyl)-4-heptylbicyclo[2.2.2]octane. 1-(4-[(E)-Pent-2-enyloxy]phenyl)-4-heptylbicyclo[2.2.2]octane. 1-(4-[(E)-Hex-2-enyloxy]phenyl)-4-heptylbicyclo[2.2.2]octane. 1-(4-[(E)-Hept-2-enyloxy]phenyl)-4-heptylbicyclo[2.2.2]octane. 1-(4-[(E)-Oct-2-enyloxy]phenyl)-4-heptylbicyclo[2.2.2]octane. 1-(4-[(Z)-Hex-3-enyloxy]phenyl)-4-pentylbicyclo[2.2.2]octane. 1-(4-[(E)-Hex-4-enyloxy]phenyl)-4-pentylbicyclo[2.2.2]octane. 1-(4-[Hex-5-enyloxy]phenyl)-4-pentylbicyclo[2.2.2]octane. 1-(4'-[(E)-But-2-enyloxy]biphenyl-4-yl)-4-propylbicyclo[2.2.2]octane. 1-(4'-[(E)-Pent-2-enyloxy]biphenyl-4-yl)-4-propylbicyclo[2.2.2]octane. 1-(4'-[(E)-Hex-2-enyloxy]biphenyl-4-yl)-4-propylbicyclo[2.2.2]octane. 1-(4'-[(E)-Hept-2-enyloxy]biphenyl-4-yl)-4-propylbicyclo[2.2.2]octane. 1-(4'-[(E)-Oct-2-enyloxy]biphenyl-4-yl)-4-propylbicyclo[2.2.2]octane. 1-(4'-[(E)-But-2-enyloxy]biphenyl-4-yl)-4-pentylbicyclo[2.2.2]octane. 1-(4'-[(E)-Pent-2-enyloxy]biphenyl-4-yl)-4-pentylbicyclo[2.2.2]octane. 1-(4'-[(E)-Hex-2-enyloxy]biphenyl-4-yl)-4-pentylbicyclo[2.2.2]octane. 1-(4'-[(E)-Hept-2-enyloxy]biphenyl-4-yl)-4-pentylbicyclo[2.2.2]octane. 1-(4'-[(E)-Oct-2-enyloxy]biphenyl-4-yl)-4-pentylbicyclo[2.2.2]octane. 1-(4'-[(Z)-Hex-3-enyloxy]biphenyl-4-yl)-4-pentylbicyclo[2.2.2]octane. 1-(4'-[(E)-Hex-4-enyloxy]biphenyl-4-yl)-4-pentylbicyclo[2.2.2]octane. 1-(4'-[Hex-5-enyloxy]biphenyl-4-yl)-4-pentylbicyclo[2.2.2]octane. 1-(4'-[(E)-But-2-enyloxy]biphenyl-4-yl)-4-heptylbicyclo[2.2.2]octane. 1-(4'-[(E)-Pent-2-enyloxy]biphenyl-4-yl)-4-heptylbicyclo[2.2.2]octane. 1-(4'-[(E)-Hex-2-enyloxy]biphenyl-4-yl)-4-heptylbicyclo[2.2.2]octane. 1-(4'-[(E)-Hept-2-enyloxy]biphenyl-4-yl)-4-heptylbicyclo[2.2.2]octane. 1-(4'-[(E)-Oct-2-enyloxy]biphenyl-4-yl)-4-heptylbicyclo[2.2.2]octane.

EXAMPLE 2
Preparation of 4-(4-pentylbicyclo[2.2.2]octyl)phenyl (E)-hex-2-enoate.

A solution of N,N-dicyclohexylcarbodiimide (0.22 g, 1.1 mmol) in dichloromethane (10 cm$^3$) was added to a solution of (E)-hex-2-enoic acid (0.10 g, 0.9 mmol) 4-(4-pentylbicyclo[2.2.2]octyl)phenol (0.24 g, 0.9 mmol), 4-(dimethylamino)pyridine (0.04 g) in dichloromethane (20 cm$^3$), cooled in an ice bath (0° C.) under an atmosphere of nitrogen. The reaction mixture was stirred overnight, filtered to remove precipitated material and the filtrate was evaporated down under reduced pressure. The crude product was purified by column chromatography on silica gel using a 9:1 petroleum ether (40–60° C./ethyl acetate mixture as eluent, followed by recrystallization from ethanol to yield 0.13 g (40%), K 70° C., N-I 134° C.

The following compounds could be obtained analogously:
4-(4-Propylbicyclo[2.2.2]octyl)phenyl (E)-but-2-enoate. 4-(4-Propylbicyclo[2.2.2]octyl)phenyl (E)-pent-2-enoate. 4-(4-Propylbicyclo[2.2.2]octyl)phenyl (E)-hex-2-enoate. 4-(4-Propylbicyclo[2.2.2]octyl)phenyl (E)-hept-2-enoate. 4-(4-Propylbicyclo[2.2.2]octyl)phenyl (E)-oct-2-enoate. 4-(4-Pentylbicyclo[2.2.2]octyl)phenyl (E)-but-2-enoate, K 76° C., N-I 154° C. 4-(4-Pentylbicyclo[2.2.2]octyl)phenyl (E)-pent-2-enoate, K 72° C., N-I 130° C. 4-(4-Pentylbicyclo[2.2.2]octyl)phenyl (E)-hept-2-enoate, K 49° C., N-I 121° C. 4-(4-Pentylbicyclo[2.2.2]octyl)phenyl (E)-oct-2-enoate, K 63° C., N-I 122° C. 4-(4-Heptylbicyclo[2.2.2]octyl)phenyl (E)-but-2-enoate. 4-(4-Heptylbicyclo[2.2.2]octyl)phenyl (E)-pent-2-enoate. 4-(4-Heptylbicyclo[2.2.2]octyl)phenyl (E)-hex-2-enoate. 4-(4-Heptylbicyclo[2.2.2]octyl)phenyl (E)-hept-2-enoate. 4-(4-Heptylbicyclo[2.2.2]octyl)phenyl (E)-oct-2-enoate. 4-(4-Hexylbicyclo[2.2.2]octyl)phenyl (Z)-hex-3-enoate. 4-(4-Hexylbicyclo[2.2.2]octyl)phenyl (E)-hex-4-enoate. 4-(4-Hexylbicyclo[2.2.2]octyl)phenyl hex-5-enoate. 4-(4-Propylbicyclo[2.2.2]octyl)phenyl-4'-yl (E)-but-2-enoate. 4-(4-Propylbicyclo[2.2.2]octyl)biphenyl-4'-yl (E)-pent-2-enoate. 4-(4-Propylbicyclo[2.2.2]octyl)biphenyl-4'-yl (E)-hex-2-enoate. 4-(4-Propylbicyclo[2.2.2]octyl)biphenyl-4'-yl (E)-hept-2-enoate. 4-(4-Propylbicyclo[2.2.2]octyl)biphenyl-4'-yl (E)-oct-2-enoate. 4-(4-Pentylbicyclo[2.2.2]octyl)biphenyl-4'-yl (E)-but-2-enoate. 4-(4-Pentylbicyclo[2.2.2]octyl)biphenyl-4'-yl (E)-pent-2-enoate. 4-(4-Pentylbicyclo[2.2.2]octyl)biphenyl-4'-yl (E)-hex-2-enoate. 4-(4-Pentylbicyclo[2.2.2]octyl)biphenyl-4'-yl (E)-hept-2-enoate. 4-(4-Pentylbicyclo[2.2.2]octyl)biphenyl-4'-yl (E)-oct-2-enoate. 4-(4-Pentylbicyclo[2.2.2]octyl)biphenyl-4'-yl (Z)-hex-3-enoate. 4-(4-Pentylbicyclo[2.2.2]octyl)biphenyl-4'-yl (E)-hex-4-enoate. 4-(4-Pentylbicyclo[2.2.2]octyl)biphenyl-4'-yl hex-5-enoate. 4-(4-Heptylbicyclo[2.2.2]octyl)biphenyl-4'-yl (E)-but-2-enoate. 4-(4-Heptylbicyclo[2.2.2]octyl)biphenyl-4'-yl (E)-pent-2-enoate. 4-(4-Heptylbicyclo[2.2.2]octyl)biphenyl-4'-yl (E)-hex-2-enoate. 4-(4-Heptylbicyclo[2.2.2]octyl)biphenyl-4'-yl (E)-hept-2-enoate. 4-(4-Heptylbicyclo[2.2.2]octyl)biphenyl-4'-yl (E)-oct-2-enoate. 1-[4-(trans-5-[(E)-But-2-enoyloxy]dioxan-2-yl)phenyl]-4-pentylbicyclo[2.2.2]octane. 1-[4-(trans-5-[(E)-Pent-2-enoyloxy]dioxan-2-yl)phenyl]-4-pentylbicyclo[2.2.2]octane. 1-[4-(trans-5-[(E)-Hept-2-enoyloxy]dioxan-2-yl)phenyl]-4-pentylbicyclo[2.2.2]octane. 1-[4-(trans-5-[(E)-Oct-2-enoyloxy]dioxan-2-yl)phenyl]-4-pentylbicyclo[2.2.2]octane. 1-[4-(trans-5-[(Z)-Hex-3-enoyloxy]dioxan-2-yl)phenyl]-4-pentylbicyclo[2.2.2]octane. 1-[4-(trans-5-[(E)-Hex-4-enoyloxy]dioxan-2-yl)phenyl]-4-pentylbicyclo[2.2.2]octane. 1-[4-(trans-5-[Hex-5-enoyloxy]dioxan-2-yl)phenyl]-4-pentylbicyclo[2.2.2]octane.

EXAMPLE 3
Preparation of 1-[4-(trans-4-[(E)-hex-2-enyloxy]cyclohexyl)phenyl]-4-pentylbicyclo[2.2.2]octane A mixture of toluene-4-sulfonic acid (E)-hex-2-en-1-yl ester (1.0 g, 2.8 mmol), 1-[4-(trans-4-hydroxycyclohexyl)phenyl]-4-pentylbicyclo[2.2.2]octane (0.50 g, 1.4 mmol), potassium tert-butoxide (0.55 g, 4.5 mmol) and 1,2-dimethoxyethane (20 cm$^3$) is stirred at room temperature overnight, filtered to remove inorganic material diluted with water (100 cm$^3$) and then extracted into diethyl ether (3×50 cm$^3$). The combined organic extracts are washed with water (2×100 cm$^3$), dried (MgSO$_4$), filtered and then evaporated down. The residue is purified by column chromatography on silica gel using a 9:1 hexane/ethyl acetate mixture as eluent and recrystallisation from ethanol to yield 0.25 g (66%) of the desired ether.

The toluene-4-sulfonic acid (E)-hex-2-en-1-yl ester and 1-[4-(trans-4-hydroxycyclohexyl) phenyl]-4-pentylbicyclo[2.2.2]octane required as starting materials could be prepared as follows:

(a). A solution of toluene-4-sulfonyl chloride (0.75 g, 4.0 mmol) in dichloromethane (10 cm$^3$) is added slowly to a solution of (E)-hex-2-en-1-ol (0.39 g, 4.0 mmol), triethylamine (0.80 g, 8.0 mmol) and dichloromethane (50 cm$^3$) at 0° C. The reaction mixture is stirred at 0° C. for 6 h, washed with dilute hydrochloric acid (2×50 cm³), water (2×50 cm³) and dilute sodium carbonate solution (2×50 cm³), dried (MgSO$_4$), filtered and then evaporated down to yield 1.0 g (99%) of the desired tosylate, which is used without further purification.

(b). A solution of 1-bromo-4-pentylbicyclo[2.2.2]octane (6 g, 23 mmol) in sieve-dried nitrobenzene (100 cm³) is added dropwise to a stirred solution of 4-phenylcyclohexanone (3.9 g, 23 mmol) and anhydrous iron(III)chloride (1.2 g, 9 mmol) in sieve-dried nitrobenzene (100 cm³) maintained at 80° C. through the addition and overnight. The cooled solution is added to a small volume of hydrochloric acid and stirred for 20 min. The organic layer is separated off and steam-distilled to yield a solid residue. This is taken up in dichloromethane and dried (MgSO$_4$). The raw product is crystallised from ethanol to yield the desired 4-[4-(4-pentylbicyclo[2.2.2]octyl)phenyl] cyclohexanone (5.4 g, 69%).

(c). 4-[4-(4-pentylbicyclo[2.2.2]octyl)penyl] cyclohexanone (1.5 g, 4.3 mmol) and a mixture of 9:1 methanol/ether (25 cm³) is added dropwise to a freshly prepared mixture of sodium borohydride (1.2 g, 8.5 mmol) and a mixture of 9:1 methanol/ether (25 cm³) at 0° C. When the addition is complete, the reaction mixture is stirred overnight at room temperature. A 25 per cent hydrochloric acid solution is added carefully to the reaction mixture, which was extracted into ethyl acetate (3×50 cm³). The combined organic extracts are washed with water (2×500 ml) and dilute sodium carbonate solution (2×500 ml), dried (MgSO$_4$), filtered and then evaporated down. The residue is purified by column chromatography on silica gel using a 7:3 hexane/ethyl acetate mixture as eluent and recrystallisation from ethanol to yield the pure 1-[4-(trans-4-hydroxycyclohexyl)phenyl]-4-pentylbicyclo[2.2.2] octane (1.2 g, 80 per cent).

The following compounds could be obtained analogously:
1-[4-(trans-4[(E)-But-2-enyloxy]cyclohexyl)phenyl]-4-propylbicyclo[2.2.2]octane. 1-[4-(trans-4-[(E)-Pent-2-enyloxy]cyclohexyl)phenyl]-4-propylbicyclo[2.2.2]octane. 1-[4-(trans-4-[(E)-Hept-2-enyloxy]cyclohexyl)phenyl]-4-propylbicyclo[2.2.2]octane. 1-[4-(trans-4-[(E)-Oct-2-enyloxy]cyclohexyl)phenyl]-4-propylbicyclo[2.2.2]octane. 1-[4-(trans-4-[(E)-But-2-enyloxy]cyclohexyl)phenyl]-4-pentylbicyclo[2.2.2]octane. 1-[4-(trans-4-[(E)-Pent-2-enyloxy]cyclohexyl)phenyl]-4-pentylbicyclo[2.2.2]octane. 1-[4-(trans-4-[(E)-Hept-2-enyloxy]cyclohexyl)phenyl]-4-pentylbicyclo[2.2.2]octane. 1-[4-(trans-4-[(E)-Oct-2-enyloxy]cyclohexyl)phenyl]-4-pentylbicyclo[2.2.2]octane. 1-[4-(trans-4-[(Z)-Hex-3-enyloxy]cyclohexyl)phenyl]-4-pentylbicyclo[2.2.2]octane. 1-[4-(trans-4-[(E)-Hex-4-enyloxy]cyclohexyl)phenyl]-4-pentylbicyclo[2.2.2]octane. 1-[4-(trans-4-[Hex-5-enyloxy]cyclohexyl)phenyl]-4-pentylbicyclo[2.2.2]octane. 1-[4-(trans-4-[(E)-But-2-enyloxy]cyclohexyl)phenyl]-4-heptylbicyclo[2.2.2]octane. 1-[4-(trans-4-[(E)-Pent-2-enyloxy]cyclohexyl)phenyl]-4-heptylbicyclo[2.2.2]octane. 1-[4-(trans-4-[(E)-Hept-2-enyloxy]cyclohexyl)phenyl]-4-heptylbicyclo[2.2.2]octane. 1-[4-(trans-4-[(E)-Oct-2-enyloxy]cyclohexyl)phenyl]-4-heptylbicyclo[2.2.2]octane.

EXAMPLE 4

Preparation of trans-4-[4-(4-pentylbicyclo[2.2.2]octyl) phenyl]cyclohexyl (E)-hex-2-enoate A solution of N,N-dicyclohexylcarbodiimide (0.22 g, 1.1 mmol) in dichloromethane (10 cm³) is added to a solution of (E)-hex-2-enoic acid (0.10 g, 0.9 mmol), 1-[4-(trans-4-hydroxycyclohexyl) phenyl]-4-pentylbicyclo[2.2.2]octane (0.32 g, 0.9 mmol), 4-(dimethylamino) pyridine (0.04 g) in dichloromethane (20 cm³), cooled in an ice bath (0° C.) under an atmosphere of nitrogen. The reaction mixture is stirred overnight, filtered to remove precipitated material and the filtrate is evaporated down under reduced pressure. The crude product is purified by column chromatography on silica gel using a 9:1 petroleum ether (40–60° C.)/ethyl acetate mixture as eluent, followed by recrystallization from ethanol to yield the desired ester (0.26 g, 64%).

The following compounds could be obtained analogously: trans-4-[4-(4-Pentylbicyclo[2.2.2]octyl)phenyl]cyclohexyl (E)-but-2-enoate. trans-4-[4-(4-Pentylbicyclo[2.2.2]octyl) phenyl]cyclohexyl (E)-pent-2-enoate. trans-4-[4-(4-Pentylbicyclo[2.2.2]octyl)phenyl]cyclohexyl (E)-hept-2-enoate. trans-4-[4-(4-Pentylbicyclo[2.2.2]octyl)phenyl] cyclohexyl (E)-oct-2-enoate. trans-4-[4-(4-Pentylbicyclo [2.2.2]octyl)phenyl]cyclohexyl (Z)-hex-3-enoate. trans-4-[4-(4-Pentylbicyclo[2.2.2]octyl)phenyl]cyclohexyl (E)-hex-4-enoate. trans-4-[4-(4-Pentylbicyclo[2.2.2]octyl)phenyl] cyclohexyl hex-5-enoate.

EXAMPLE 5

Preparation of 1-[4-(5-[(E)-hex-2-enyloxy]pyrimidin-2-yl) phenyl]-4-pentylbicyclo [2.2.2]octane.

Triphenylphosphine (0.34 g, 1.3 mmol) is added in small portions to a solution of (E)-hex-2-Triphenylphosphine (0.34 g, 1.3 mmol), 1-[4-(5-hydroxypyrimidin-2-yl)phenyl]-4-pentylbicyclo [2.2.2]octane (0.38 g, 1.3 mmol), diethylazodicarboxylate (0.22 g, 1.3 mmol) in dry tetrahydrofuran (20 cm³), cooled in an ice bath under an atmospher of nitrogen. The reaction mixture is stirred at room temperature overnight. The solvent is removed under reduced pressure and the crude product is purified by column chromatography on silica gel using a 9:1 petroleum ether (40–60° C.)/ethyl acetate mixture as eluent, followed by recrystallisation from ethanol to yield 0.24 g (44%) of the ether.

The 1-[4-(5-hydroxypyrimidin-2-yl)phenyl]-4-pentylbicyclo[2.2.2]octane required as starting material could be prepared as follows:

(a). A solution of 4-(4-pentylbicyclo[2.2.2]octyl) benzonitrile (50.0 g, 170 mmol) in ethanol (35 cm³) and toluene (200 cm³) is saturated with hydrogen chloride at 0° C. and then stirred at room temperature for 2 days. The reaction mixture is evaporated down under reduced pressure, shaken with ether (500 cm³), filtered, washed with portions of ether and finally dried under vacuum to yield 57.6 g (89%) of 4-(4-pentylbicyclo [2.2.2]octyl)phenylimidoethylether hydrochloride.

(b). A saturated ethanolic ammonia solution 350 cm³) is added to a solution of 4-(4-pentylbicyclo [2.2.2]octyl) phenylimidoethylether hydrochloride (57.6 g, 153 mmol) and ethanol (350 cm³). The reaction mixture is stirred at room temperature for 2 days and then evaporated. The solid residue is shaken with ether (500 cm³), filtered, washed with portions of ether and finally dried under vacuum to yield 50.2 g (94%) of 4-(4-pentylbicyclo [2.2.2]octyl)benzamidine hydrochloride.

(c). A 5.4 molar solution of sodium methoxide in methanol (40 cm³) is added dropwise to a mixture of (4-[benzyloxy]phenyl)-(2-methoxymethylidene)ethanal (146 mmol), 4-(4-pentylbicyclo [2.2.2]octyl) benzamidine hydrochloride (50.2 g, 146 mmol) and methanol (160 cm³) at room temperature, stirred overnight and added to water an extracted with dichloromethane (3×100 cm³). The combined organic layers are washed with water (500 cm³), dilute potassium carbonate (200 cm³) and once again with water (500 cm³) then dried (mgSO₄), filtered and evaporated. The residue is purified by column chromatography (flash) on silica gel using a 97:3 dichloromethane/methanol mixture as eluent followed by recrystallisation from ethyl acetate to yield the desired ether (38.5 g, 70%).

(d). A one molar solution of boron tribromide (120 cm³) is added dropwise to a solution 1-[4-(5-benzyloxypyrimidin-2-yl) phenyl]-4-pentylbicyclo [2.2.2]octane (38.5 g, 100 mmol) in dichloromethane (200 cm³) and cooled using an ice bath. The reaction is stirred overnight at room temperature and then poured onto an ice/water mixture (500 g). The organic layer is separated off and the aqueous layer extracted with dichloromethane (3×100 cm³). The combined organic layers are washed with water (500 cm³), dilute potassium carbonate (200 cm³) and once again with water (500 cm³) then dried (MgSO₄), filtered and evaporated. The residue is purified by column chromatography (flash) on silica gel using a 97:3 dichloromethane/methanol mixture as eluent followed by recrystallisation from ethyl acetate to give the 1-[4-(5-hydroxypyrimidin-2-yl)phenyl]-4-pentylbicyclo[2.2.2] octane (14.7 g, 50%).

The following compounds could be obtained analogously: 1-[4-(5-[(E)-But-2-enyloxy]pyrimidin-2-yl)phenyl]-4-propylbicyclo[2.2.2]octane. 1-[4-(5-[(E)-Pent-2-enyloxy]pyrimidin-2-yl)phenyl]-4-propylbicyclo[2.2.2]octane. 1-[4-(5-[(E)-Hex-2-enyloxy]pyrimidin-2-yl)phenyl]-4-propylbicyclo[2.2.2]octane. 1-[4-(5-[(E)-Hept-2-enyloxy]pyrimidin-2-yl)phenyl]-4-propylbicyclo[2.2.2]octane. 1-[4-(5-[(E)-Oct-2-enyloxy]pyrimidin-2-yl)phenyl]-4-propylbicyclo[2.2.2]octane. 1-[4-(5-[(E)-But-2-enyloxy]pyrimidin-2-yl)phenyl]-4-pentylbicyclo[2.2.2]octane. 1-[4-(5-[(E)-Pent-2-enyloxy]pyrimidin-2-yl)phenyl]-4-pentylbicyclo[2.2.2]octane. 1-[4-(5-[(E)-Hept-2-enyloxy]pyrimidin-2-yl)phenyl]-4-pentylbicyclo[2.2.2]octane. 1-[4-(5-[(E)-Oct-2-enyloxy]pyrimidin-2-yl)phenyl]-4-heptylbicyclo[2.2.2]octane. 1-[4-(5-[(E)-But-2-enyloxy]pyrimidin-2-yl)phenyl]-4-heptylbicyclo[2.2.2]octane. 1-[4-(5-[(E)-Pent-2-enyloxy]pyrimidin-2-yl)phenyl]-4-heptylbicyclo[2.2.2]octane. 1-[4-(5-[(E)-Hex-2-enyloxy]pyrimidin-2-yl)phenyl]-4-heptylbicyclo[2.2.2]octane. 1-[4-(5-[(E)-Hept-2-enyloxy]pyrimidin-2-yl)phenyl]-4-heptylbicyclo[2.2.2]octane. 1-[4-(5-[(E)-Oct-2-enyloxy]pyrimidin-2-yl)phenyl]-4-heptylbicyclo[2.2.2]octane.

EXAMPLE 6

Preparation of 2-[4-(4-pentylbicyclo[2.2.2]octyl)phenyl] pyrimidin-5-yl (E)-hex-2-enoate A solution of N,N-dicyclohexylcarbodiimide (0.22 g, 1.1 mmol) in dichloromethane (10 cm³) is added to a solution of (E)-hex-2-enoic acid (0.10 g, 0.9 mmol), 1-[4-(5-hydroxypyrimidin-2-yl) phenyl]-4-pentylbicyclo[2.2.2] octane (0.25 g, 0.9 mmol), 4-(dimethylamino)pyridine (0.04 g) in dichloromethane (20 cm³), cooled in an ice bath (0° C.) under an atmosphere of nitrogen. The reaction mixture is stirred overnight, filtered to remove precipitated material and the filtrate is evaporated down under reduced pressure. The crude product is purified by column chromatography on silica gel using a 9:1 petroleum ether (40–60° C.)/ethyl acetate mixture as eluent, followed by recrystallisation from ethanol to yield the desired ester (0.15 g, 45%).

The following compounds could be obtained analogously: 2-[4-(4-Propylbicyclo[2.2.2]octyl)phenyl]pyrimidin-5-yl (E)-but-2-enoate. 2-[4-(4-Propylbicyclo[2.2.2]octyl)phenyl] pyrimidin-5-yl (E)-pent-2-enoate. 2-[4-(4-Propylbicyclo [2.2.2]octyl)phenyl]pyrimidin-5-yl (E)-hex-2-enoate. 2-[4-(4-Propylbicyclo[2.2.2]octyl)phenyl]pyrimidin-5-yl (E)-hept-2-enoate. 2-[4-(4-Propylbicyclo[2.2.2]octyl)phenyl] pyrimidin-5-yl (E)-oct-2-enoate. 2-[4-(4-Pentylbicyclo [2.2.2]octyl)phenyl]pyrimidin-5-yl (E)-but-2-enoate. 2-[4-(4-Pentylbicyclo[2.2.2]octyl)phenyl]pyrimidin-5-yl (E)-pent-2-enoate. 2-[4-(4-Pentylbicyclo[2.2.2]octyl)phenyl] pyrimidin-5-yl (E)-hept-2-enoate. 2-[4-(4-Pentylbicyclo [2.2.2]octyl)phenyl]pyrimidin-5-yl (E)-oct-2-enoate. 2-[4-(4-Heptylbicyclo[2.2.2]octyl)phenyl]pyrimidin-5-yl (E)-but-2-enoate. 2-[4-(4-Heptylbicyclo[2.2.2]octyl)phenyl] pyrimidin-5-yl (E)-pent-2-enoate. 2-[4-(4-Heptylbicyclo [2.2.2]octyl)phenyl]pyrimidin-5-yl (E)-hex-2-enoate. 2-[4-(4-Heptylbicyclo[2.2.2]octyl)phenyl]pyrimidin-5-yl (E)-hept-2-enoate. 2-[4-(4-Heptylbicyclo[2.2.2]octyl)phenyl] pyrimidin-5-yl (E)-oct-2-enoate.

EXAMPLE 7

Preparation of 1-[4-(trans-5-[(E)-hex-2-enyloxy]dioxan-2-yl)phenyl]-4-pentylbicyclo [2.2.2]octane.

A mixture of toluene-4-sulfonic acid (E)-hex-2-en-1-yl ester (1.0 g, 2.8 mmol), 1-[4-(trans-5-hydroxydioxan-2-yl) phenyl]-4-pentylbicyclo[2.2.2]octane (0.50 g, 1.4 mmol), potassium tert-butoxide (0.55 g, 4.5 mmol) and 1,2-dimethoxyethane (50 cm³) is stirred at room temperature overnight, filtered to remove inorganic material, diluted with water (500 cm³) and then extracted into diethyl ether (3×100 cm³). The combined organic extracts are washed with water (2×500 cm³), dried (MgSO₄), filtered and then evaporated down. The residue is purified by column chromatography on silica gel using a 9:1 hexane/ethyl acetate mixture as eluent and recrystallisation from ethanol to yield 0.25 g (66%) of the desired ether.

The 1-[4-(trans-5-hydroxydioxan-2-yl)phenyl]-4-pentylbicyclo[2.2.2]octane required as starting materials could be prepared as follows:

(a). A solution of diisobutyl aluminium hydride (20% v/v) in toluene (100 cm³) is added dropwise to a solution of 4-(4-pentylbicyclo[2.2.2]octyl)benzonitrile (5.5 g, 45 mmol) at 0° C. After completion of the addition the reaction solution is allowed to regain room temperature slowly and is stirred at this temperature overnight. The reaction solution is cooled to 0° C. and cold 1N sulphuric acid (500 cm³) is added carefully. The organic phase is separated off and the aqueous phase extracted with toluene (3×100 cm³). The combined organic phases are washed with water (2×100 cm³), dried (MgSO₄) and finally evaporated down under reduced pressure. The residue is purified by recrystallisation from ethyl acetate to give 2.5 g (45%) of the pure aldehyde.

(b). A solution of 4-(4-pentylbicyclo[2.2.2]octyl) benzaldehyde (2.5 g, 8.5 mmol), glycerol (1.0 g, 8.5 mmol), pyridinium-(toluyl-4-sulphonate) (0.2 g) and toluene is heated for over 2 h so that the toluene/water mixture generated is continuously distilled off. The solution is evaporated down and the residue purified by column chromatography on silica gel using a 7:3 hexane/ethyl acetate mixture as eluent and recrystallisation from ethanol to yield 0.75 g (25%) of the 1-[4-(trans-5-hydroxydioxan-2-yl)phenyl]-4-pentylbicyclo[2.2.2]octane.

The following compounds could be obtained analogously: 1-[4-(trans-5-[(E)-But-2-enyloxy]dioxan-2-yl)phenyl]-4-propylbicyclo[2.2.2]octane. 1-[4-(trans-5-[(E)-Pent-2-enyloxy]dioxan-2-yl)phenyl]-4-propylbicyclo[2.2.2]octane.

1-[4-(trans-5-[(E)-Hept-2-enyloxy]dioxan-2-yl)phenyl]-4-propylbicyclo[2.2.2]octane. 1-[4-(trans-5-[(E)-Oct-2-enyloxy]dioxan-2-yl)phenyl]-4-propylbicyclo[2.2.2]octane. 1-[4-(trans-5-[(E)-But-2-enyloxy]dioxan-2-yl)phenyl]-4-pentylbicyclo[2.2.2]octane. 1-[4-(trans-5-[(E)-Pent-2-enyloxy]dioxan-2-yl)phenyl]-4-pentylbicyclo[2.2.2]octane. 1-[4-(trans-5-[(E)-Hept-2-enyloxy]dioxan-2-yl)phenyl]-4-pentylbicyclo[2.2.2]octane. 1-[4-(trans-5-[(E)-Oct-2-enyloxy]dioxan-2-yl)phenyl]-4-pentylbicyclo[2.2.2]octane. 1-[4-(trans-5-[(Z)-Hex-3-enyloxy]dioxan-2-yl)phenyl]-4-pentylbicyclo[2.2.2]octane. 1-[4-(trans-5-[(E)-Hex-4-enyloxy]dioxan-2-yl)phenyl]-4-pentylbicyclo[2.2.2]octane. 1-[4-(trans-5-[Hex-5-enyloxy]dioxan-2-yl)phenyl]-4-pentylbicyclo[2.2.2]octane. 1-[4-(trans-5-[(E)-But-2-enyloxy]dioxan-2-yl)phenyl]-4-heptylbicyclo[2.2.2]octane. 1-[4-(trans-5-[(E)-Pent-2-enyloxy]dioxan-2-yl)phenyl]-4-heptylbicyclo[2.2.2]octane. 1-[4-(trans-5-[(E)-Hept-2-enyloxy]dioxan-2-yl)phenyl]-4-heptylbicyclo[2.2.2]octane. 1-[4-(trans-5-[(E)-Oct-2-enyloxy]dioxan-2-yl)phenyl]-4-heptylbicyclo[2.2.2]octane.

EXAMPLE 8

Preparation of trans-2-[4-(4-pentylbicyclo[2.2.2]octyl)phenyl]dioxan-5-yl (E)-hex-2-enoate A solution of N,N-dicyclohexylcarbodiimide (0.18 g, 0.8 mmol) in dichloromethane (10 cm$^3$) is added to a solution of (E)-hex-2-enoic acid (0.07 g, 0.7 mmol), 1-[4-(trans-5-hydroxydioxan-2-yl) phenyl]-4-pentylbicyclo[2.2.2]octane (0.25 g, 0.7 mmol), 4-(dimethylamino) pyridine (0.04 g) in dichloromethane (20 cm$^3$), cooled in an ice bath (0° C.) under an atmosphere of nitrogen. The reaction mixture is stirred overnight, filtered to remove precipitated material and the filtrate was evaporated down under reduced pressure. The crude product is purified by column chromatography on silica gel using a 9:1 petroleum ether (40–60° C.)/ethyl acetate mixture as eluent, followed by recrystallisation from ethanol to yield the desired ester.

The following compounds could be obtained analogously: trans-2-[4-(4-Propylbicyclo[2.2.2]octyl)phenyl]dioxan-5-yl (E)-but-2-enoate. trans-2-[4-(4-Propylbicyclo[2.2.2]octyl)phenyl]dioxan-5-yl (E)-pent-2-enoate. trans-2-[4-(4-Propylbicyclo[2.2.2]octyl)phenyl]dioxan-5-yl (E)-hex-2-enoate. trans-2-[4-(4-Propylbicyclo[2.2.2]octyl)phenyl]dioxan-5-yl (E)-hept-2-enoate. trans-2-[4-(4-Propylbicyclo[2.2.2]octyl)phenyl]dioxan-5-yl (E)-oct-2-enoate. trans-2-[4-(4-Pentylbicyclo[2.2.2]octyl)phenyl]dioxan-5-yl (E)-but-2-enoate. trans-2-[4-(4-Pentylbicyclo[2.2.2]octyl)phenyl]dioxan-5-yl (E)-pent-2-enoate. trans-2-[4-(4-Pentylbicyclo[2.2.2]octyl)phenyl]dioxan-5-yl (E)-hept-2-enoate. trans-2-[4-(4-Pentylbicyclo[2.2.2]octyl)phenyl]dioxan-5-yl (E)-oct-2-enoate. trans-2-[4-(4-Pentylbicyclo[2.2.2]octyl)phenyl]dioxan-5-yl (Z)-hex-3-enoate. trans-2-[4-(4-Pentylbicyclo[2.2.2]octyl)phenyl]dioxan-5-yl (E)-hex-4-enoate. trans-2-[4-(4-Pentylbicyclo[2.2.2]octyl)phenyl]dioxan-5-yl hex-5-enoate. trans-2-[4-(4-Heptylbicyclo[2.2.2]octyl)phenyl]dioxan-5-yl (E)-but-2-enoate. trans-2-[4-(4-Heptylbicyclo[2.2.2]octyl)phenyl]dioxan-5-yl (E)-pent-2-enoate. trans-2-[4-(4-Heptylbicyclo[2.2.2]octyl)phenyl]dioxan-5-yl (E)-hex-2-enoate. trans-2-[4-(4-Heptylbicyclo[2.2.2]octyl)phenyl]dioxan-5-yl (E)-hept-2-enoate. trans-2-[4-(4-Heptylbicyclo[2.2.2]octyl)phenyl]dioxan-5-yl (E)-oct-2-enoate.

EXAMPLE 9

Preparation of 1-(2, 3-difluoro-4-[(E)-hex-2-enyloxy]phenyl)-4-pentylbicyclo[2.2.2]octane Triphenylphosphine (0.34 g, 1.3 mmol) is added in small portions to a solution of (E)-hex-2-en-1-ol (0.13 g, 1.3 mmol), 2, 3-difluoro-4-(4-pentylbicyclo[2.2.2]octyl)phenyl (0.40 g, 1.3 mmol), diethylazodicarboxylate (0.22 g, 1.3 mmol) in dry tetrahydrofuran (20 cm$^3$), cooled in an ice bath under an atmosphere of nitrogen. The reaction mixture is stirred at room temperature overnight. The solvent is removed under reduced pressure and the crude product is purified by column chromatography on silica gel using a 9:1 petroleum ether (40–60° C.)/ethyl acetate mixture as eluent, followed by recrystallisation from ethanol to yield 0.22 g (43%).

(a). A solution of 1-bromo-4-pentylbicyclo[2.2.2]octane (6 g, 23 mmol) in sieve-dried nitrobenzene (100 cm$^3$) is added dropwise to a stirred solution of 2, 3-difluoro-4-methoxybenzene (6 g, 23 mmol) and anhydrous iron(III)chloride (1.2 g, 9 mmol) in sieve-dried nitrobenzene (100 cm$^3$) maintained at 80° C. throughout the addition and overnight. The cooled solution is added to a small volume of hydrochloric acid and stirred for 20 min. The organic layer is separated off and steam-distilled to yield a solid residue. This is taken up in dichloromethane and dried (MgSO$_4$). The raw product is crystallised from ethanol to yield the desired 2, 3-difluoro-1-methoxy-4-(4-pentylbicyclo[2.2.2]octyl)benzene (3.2 g, 44%)

(b). A one molar solution of boron tribromide (10 cm$^3$) is added dropwise to a solution of 2, 3-difluoro-1-methoxy-4-(4-pentylbicyclo[2.2.2]octyl)benzene (3.2 g, 1.0 mmol) in dichloromethane (50 cm$^3$) and cooled using an ice bath. The reaction is stirred overnight at room temperature and then poured onto an ice/water mixture (100 g). The organic layer is separated off and the aqueous layer extracted with dichloromethane (3×50 cm$^3$). The combined organic layers are washed with water (100 cm$^3$), dilute potassium carbonate (100 cm$^3$) and once again with water (100 cm$^3$) then dried (MgSO$_4$), filtered and evaporated. The residue is purified by column chromatography (flash) on silica gel using a 97:3 dichloromethane/methanol mixture as eluent followed by recrystallisation from ethyl acetate to give the phenol (yield 2.2 g, 72%).

The following compounds could be obtained analogously: 1-(4-[(E)-But-2-enyloxy]-2, 3-difluorophenyl)-4-propylbicyclo[2.2.2]octane. 1-(4-[(E)-Pent-2-enyloxy]-2, 3-difluorophenyl)-4-propylbicyclo[2.2.2]octane. 1-(4-[(E)-Hept-2-enyloxy]-2, 3-difluorophenyl)-4-propylbicyclo[2.2.2]octane. 1-(4-[(E)-Oct-2-enyloxy]-2, 3-difluorophenyl)-4-propylbicyclo[2.2.2]octane. 1-(4-[(E)-But-2-enyloxy]-2, 3-difluorophenyl)-4-pentylbicyclo[2.2.2]octane. 1-(4-[(E)-Pent-2-enyloxy]-2, 3-difluorophenyl)-4-pentylbicyclo[2.2.2]octane. 1-(4-[(E)-Hex-2-enyloxy]-2, 3-difluorophenyl)-4-pentylbicyclo[2.2.2]octane. 1-(4-[(E)-Hept-2-enyloxy]-2, 3-difluorophenyl)-4-pentylbicyclo[2.2.2]octane. 1-(4-[(E)-Oct-2-enyloxy]-2, 3-difluorophenyl)-4-pentylbicyclo[2.2.2]octane. 1-(4-[(E)-But-2-enyloxy]-2, 3-difluorophenyl)-4-heptylbicyclo[2.2.2]octane. 1-(4-[(E)-Pent-2-enyloxy]-2, 3-difluorophenyl)-4-heptylbicyclo[2.2.2]octane. 1-(4-[(E)-Hex-2-enyloxy]-2, 3-difluorophenyl)-4-heptylbicyclo[2.2.2]octane. 1-(4-[(E)-Hept-2-enyloxy]-2, 3-difluorophenyl)-4-heptylbicyclo[2.2.2]octane. 1-(4-[(E)-Oct-2-enyloxy]-2, 3-difluorophenyl)-4-heptylbicyclo[2.2.2]octane.

TABLE 1

Transition temperatures for the 1-(4-[(E)-alk-2-enoyloxy]phenyl)-4-pentylbicyclo[2.2.2]octanes

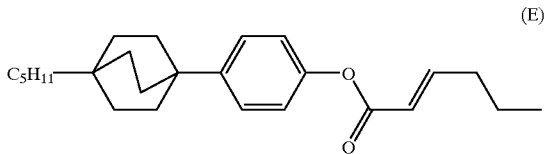

| Compound | n | C—N/° C. | N—I/° C. | $\Delta T_{NI}$/° C. |
|---|---|---|---|---|
| 1 | 1 | 76 | 154 | 78 |
| 2 | 2 | 72 | 130 | 58 |
| 3 | 3 | 70 | 134 | 64 |
| 4 | 4 | 49 | 121 | 72 |
| 5 | 5 | 63 | 122 | 59 |

TABLE 2

Transition temperatures for the 1-[4-(octanoyloxy)phenyl]-4-pentylbicyclo[2.2.2]octane and the 1-[4-([E]-oct-2-enoyloxy)phenyl]-4-pentylbicyclo[2.2.2]octanes

| Compound | R | C—N/° C. | N—I/° C. | $\Delta T_{NI}$/° C. |
|---|---|---|---|---|
| | (octanoyloxy) | 84 | 87 | 3 |
| | (E)-oct-2-enoyloxy | 63 | 122 | 59 |

TABLE 3

Transition temperatures for the bicyclo [2.2.2]octanes

| Compound | R | C—N/° C. | $S_B$-N/° C. | $S_A$-N/° C. | N—I/° C. |
|---|---|---|---|---|---|
| | (E) | 69 | — | (59) | 83 |
| | | 66 | (54) | — | 79 |

( ) represents a monotropic transition temperature

The following birefringence data was obtained:

Wt/% in ZLI3086=10
Ext Δn 30° C.=0.128
Ext Δn 20° C.=0.133
Ext Δn T/$T_{NI}$=0.8=0.128 wherein Ext Δn is a linear extrapolation in concentration of the birefringence in ZL13086 which is a commercially available (from Merck UK) apolar nematic host mixture. T is the temperature at which the measurement was taken (in Kelvin) and $T_N$ is the phase transition for the nematic-isotropic phase change (in Kelvin).

One known device in which the materials of the current invention may be incorporated is the twisted nematic device which uses a thin layer of a nematic material between glass slides. The slides are unidirectionally rubbed and assembled with the rubbing directions orthogonal. The rubbing gives a surface alignment to the liquid crystal molecules resulting in a progressive 90° twist across the layer. When placed between polarisers, with their optical axis perpendicular or parallel to a rubbing direction the device rotates the plane of polarised light in its OFF state and transmits without rotation in the ON state. Small amounts of cholesteric material may be added to the nematic material to ensure the 90° twist is of the same sense across the whole area of the device as explained in UK patents 1,472,247 and 1,478,592.

An improvement in the performance of large, complex, nematic LCDs occurred in 1982 when it was observed that the voltage dependence of the transmission of nematic LC layers with twist angles in the range 180° to 270° could become infinitely steep, see C. M. Waters, V. Brimmell and E. P. Raynes, Proc. 3rd Int. Display Res. Conf. Kobe, Japan, 1983, 396. The larger twist angles are produced by a combination of surface alignment and making the nematic mixture into a long pitch cholesteric by the addition of a small amount of a chiral twisting agent. The increasing twist angle steepens the transmission/voltage curve, until it becomes bistable for 270°0 twist; for a specific twist angle between 225° and 270°0 the curve becomes infinitely steep and well suited to multiplexing. The larger twist angles present have resulted in the name supertwisted nematic (STN) for the LCDs.

Liquid Crystal Devices describing the use of STNs may be found in patent application GB 8218821 and resulting granted patents including U.S. Pat. No. 4,596,446.

The display of FIGS. 1 and 2 comprises a liquid crystal cell 1 formed by a layer 2 of cholesteric liquid crystal material contained between glass walls 3,4. A spacer ring 5 maintains the walls typically 6 μm apart. Strip like row electrodes $6_1$ to $6_m$, e.g. of $SnO_2$ are formed on one wall 3 and similar column electrodes $7_1$ to $7_n$ formed on the other wall 4. With m-row electrodes and n-column electrodes this forms an mxn matrix of addressable elements. Each element is formed by the interaction of a row and column electrode.

A row driver supplies voltage to each row electrode 6. Similarly a column drive 9 supplies voltages to each column electrode 7. Control of applied voltages is from a control logic 10 which receives power from a voltage source 11 and timing from a clock 12.

An example of the use of a material and device embodying the present invention will now be described with reference to FIG. 2.

The liquid crystal device consists of two transparent plates, 3 and 4, for example made from glass. These plates are coated on their internal face with transparent conducting electrodes 6 and 7. An alignment layer is introduced onto the internal faces of the cell so that a planar orientation of the molecules making up the liquid crystalline material will be approximately parallel to the glass plates 3 and 4. This is done by coating the glass plates 3,4 complete with conducting electrodes so that the intersections between each column and row form an x, y matrix of addressable elements or pixels. For some types of display the alignment directions are orthogonal. Prior to the construction of the cell the alignment layers are rubbed with a roller covered in cloth (for example made from velvet) in a given direction, the rubbing directions being arranged parallel (same or opposite direction) upon construction of the cell. A spacer 5 e.g. of polymethyl methacrylate separates the glass plates 3 and 4 to a suitable distance e.g. 2 microns. Liquid crystal material 2 is introduced between glass plates 3,4 by filling the space in between them. This may be done by flow filling the cell using standard techniques. The spacer 5 is sealed with an adhesive in a vacuum using an existing technique. Polarisers 13 may be arranged in front of and behind the cell.

Alignment layers may be introduced into one or more of the cell walls by one or more of the standard surface treatment techniques such as rubbing, oblique evaporation or as described above by the use of polymer aligning layers.

In alternative embodiments the substrates with the aligning layers on them are heated and sheared to induce alignment, alternatively the substrates with the aligning layers are thermally annealed above the glass transition temperature and below the liquid crystal to isotropic phase transition in combination with an applied field. Further embodiments may involve a combination of these aligning techniques. With some of these combinations an alignment layer may not be necessary.

The device may operate in a transmissive or reflective mode. In the former, light passing through the device, e.g. from a tungsten bulb, is selectively transmitted or blocked to form the desired display. In the reflective mode a mirror, or diffuse reflector, (16) is placed behind the second polariser 13 to reflect ambient light back through the cell and two polarisers. By making the mirror partly reflecting the device may be operated both in a transmissive and reflective mode.

The alignment layers have two functions, one to align contacting liquid crystal molecules in a preferred direction and the other to give a tilt to these molecules—a so called surface tilt—of a few degrees typically around 4° or 5°. The alignment layers may be formed by placing a few drops of the polyimide on to the cell wall and spinning the wall until a uniform thickness is obtained. The polyimide is then cured by heating to a predetermined temperature for a predetermined time followed by unidirectional rubbing with a roller coated with a nylon cloth.

In an alternative embodiment a single polariser and dye material may be combined.

Cholesteric or chiral nematic liquid crystals possess a twisted helical structure which is capable of responding to a temperature change through a change in the helical pitch length. Therefore as the temperature is changed then the wavelength of the light reflected from the planar cholesteric structure will change and if the reflected light covers the visible range then distinct changes in colour occur as the temperature varies. This means that there are many possible applications including the areas of thermography and thermooptics.

The cholesteric mesophase differs from the nematic phase in that in the cholesteric phase the director is not constant in space but undergoes a helical distortion. The pitch length for the helix is a measure of the distance for the director to turn through 360°.

By definition, a cholesteric material is chiral material. Cholesteric materials may also be used in electro-optical displays as dopants, for example in twisted nematic displays where they may be used to remove reverse twist defects, they may also be used in cholesteric to nematic dyed phase change displays where they may be used to enhance contrast by preventing wave-guiding.

Thermochromic applications of cholesteric liquid crystal materials usually use thin film preparations of the cholesterogen which are then viewed against a black background. These temperature sensing devices may be placed into a number of applications involving thermometry, medical thermography, non-destructive testing, radiation sensing and for decorative purposes. Examples of these may be found in D G McDonnell in Thermotropic Liquid Crystals, Critical Reports on Applied Chemistry, Vol 22, edited by G W Gray, 1987 pp 120–44; this reference also contains a general description of thermochromic cholesteric liquid crystals.

Generally, commercial thermochromic applications require the formulation of mixtures which possess low melting points, short pitch lengths and smectic transitions just below the required temperature-sensing region. Preferably the mixture or material should retain a low melting point and high smectic-cholesteric transition temperatures.

In general, thermochromic liquid crystal devices have a thin film of cholesterogen sandwiched between a transparent supporting substrate and a black absorbing layer. One of the fabrication methods involves producing an 'ink' with the liquid crystal by encapsulating it in a polymer and using printing technologies to apply it to the supporting substrate. Methods of manufacturing the inks include gelatin microencasulation, U.S. Pat. No. 3,585,318 and polymer dispersion, U.S. Pat. Nos. 1,161,039 and 3,872,050. One of the ways for preparing well-aligned thin-film structures of cholesteric liquid crystals involves laminating the liquid crystal between two embossed plastic sheets. This technique is described in UK patent 2,143,323.

For a review of thermochromism in liquid crystals see J G Grabmaier in 'Applications of Liquid Crystals', G Meier, E Sackmann and J G Grabmaier, Springer-Verlag, Berlin and New York, 1975, pp 83–158.

The materials of the current invention may be used in many of the known devices including those mentioned in the introduction.

What is claimed is:

1. A compound of Formula I

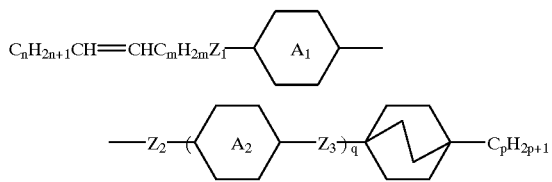

Formula I wherein
n is 1 to 5;
m is 0 to 5;
p is 1 to 5;
q is 0, 1 or 2;
$A_1$, $A_2$ are independently chosen from 1,4-disubstituted benzene, 2,5-disubstituted pyrimidine, or 2,5-disubstituted pyridine, trans-1,4-disubstituted cyclohexane, trans-2,5-disubstitued dioxane; and wherein the aromatic rings may be laterally substituted with F, Cl, Br or CN;

$Z_1$ is O, COO or OOC;

$Z_2$, $Z_3$ are independently chosen from a direct bond, COO, OOC, $C_2H_4$, $CH_2O$, $OCH_2$ or —c≡c—;

provided that when $Z_1$ is O and m is 1, 3 or 5 the carbon—carbon double bond configuration is E;

provided that when $Z_1$ is O and m is 2 or 4 the carbon—carbon double bond configuration is Z;

provided that when $Z_1$ is COO or OOC and m is 0, 2 or 4 the carbon—carbon double bond configuration is E; and provided that when $Z_1$ is COO or OOC and m is 1, 3 or 5 the carbon—carbon double bond configuration is Z.

2. A compound according to claim 1 wherein
n is 1–3; m is 1–3;
p is 3–7;
q is 0 or 1;
$A_1$ is 1,4-disubstituted benzene; $A_2$ is trans- 1,4-disubstituted cyclohexane;
$Z_1$ is O or COO; $Z_2$ and $Z_3$ are direct bonds.

3. A liquid crystal mixture comprising at least one of the compounds according to claim 1.

4. A liquid crystal mixture according to claim 3 wherein the mixture is a nematic liquid crystal mixture.

5. A liquid crystal mixture according to claim 3 wherein the mixture is a cholesteric liquid crystal mixture.

6. A device comprising two spaced cell walls each bearing electrode structures and treated on at least one facing surface with an alignment layer, a layer of a liquid crystal material enclosed between the cell walls, characterised in that it incorporates the liquid crystal mixture as claimed in claim 3.

7. A device according to claim 6 wherein the device is a twisted nematic device.

8. A device according to claim 6 wherein the device is a super-twisted nematic device.

* * * * *